(12) United States Patent
Marshik-Geurts et al.

(10) Patent No.: US 7,486,985 B2
(45) Date of Patent: Feb. 3, 2009

(54) NEAR-INFRARED SPECTROSCOPIC ANALYSIS OF BLOOD VESSEL WALLS

(75) Inventors: Barbara J. Marshik-Geurts, Methuen, MA (US); Jing Tang, Arlington, MA (US); Andres F. Zuluaga, Boston, MA (US)

(73) Assignee: InfraReDx, Inc., Cambridge, MA (US)

( * ) Notice: Subject to any disclaimer, the term of this patent is extended or adjusted under 35 U.S.C. 154(b) by 1196 days.

(21) Appl. No.: 10/212,845

(22) Filed: Aug. 5, 2002

(65) Prior Publication Data

US 2004/0024321 A1 Feb. 5, 2004

(51) Int. Cl.
*A61B 6/00* (2006.01)
(52) U.S. Cl. .................. 600/473; 600/476; 600/477; 600/478; 600/479; 382/128; 382/130
(58) Field of Classification Search ............... 600/476, 600/309, 310, 473, 478, 479, 477; 382/128, 382/130
See application file for complete search history.

(56) References Cited

U.S. PATENT DOCUMENTS

| 5,088,493 | A | * | 2/1992 | Giannini et al. | 600/323 |
| 5,197,470 | A |   | 3/1993 | Helfer et al. | 128/634 |
| 5,293,872 | A |   | 3/1994 | Alfano et al. | 128/664 |
| 5,348,002 | A | * | 9/1994 | Caro | 600/310 |
| 5,408,996 | A | * | 4/1995 | Salb | 600/317 |
| 5,441,053 | A | * | 8/1995 | Lodder et al. | 600/473 |
| 5,945,676 | A | * | 8/1999 | Khalil et al. | 250/339.12 |
| 6,272,367 | B1 | * | 8/2001 | Chance | 600/407 |
| 6,405,065 | B1 | * | 6/2002 | Malin et al. | 600/310 |
| 6,564,088 | B1 |   | 5/2003 | Soller et al. | 600/478 |
| 6,671,540 | B1 | * | 12/2003 | Hochman | 600/431 |
| 6,816,743 | B2 | * | 11/2004 | Moreno et al. | 600/473 |
| 2003/0004412 | A1 | * | 1/2003 | Izatt | 600/425 |
| 2003/0055341 | A1 | * | 3/2003 | Banerjee | 600/476 |
| 2003/0114762 | A1 | * | 6/2003 | Balas et al. | 600/476 |
| 2003/0191378 | A1 | * | 10/2003 | Davis et al. | 600/310 |
| 2003/0195401 | A1 | * | 10/2003 | Tian et al. | 600/317 |
| 2005/0054936 | A1 | * | 3/2005 | Balas | 600/476 |
| 2005/0090751 | A1 | * | 4/2005 | Balas | 600/476 |
| 2005/0119552 | A1 | * | 6/2005 | Hochman | 600/407 |
| 2006/0106293 | A1 | * | 5/2006 | Fantini | 600/323 |
| 2006/0141633 | A1 | * | 6/2006 | Balas | 436/164 |

FOREIGN PATENT DOCUMENTS

WO    WO 00/19889    4/2000

OTHER PUBLICATIONS

Moreno et al., "Detection of Lipid Pool, Thin Fibrous Cap, and Inflammatory Cells in Human Aortic Atherosclerotic Plaques by Near-Infrared Spectroscopy" *Circulation*, 105:923-927 (2002).

(Continued)

*Primary Examiner*—Brian L. Casler
*Assistant Examiner*—Sanjay Cattungal
(74) *Attorney, Agent, or Firm*—Rothwell, Figg, Ernst & Manbeck

(57) ABSTRACT

The invention relates to methods and devices for characterizing tissue in vivo, e.g., in walls of blood vessels, to determine whether the tissue is healthy or diseased.

30 Claims, 11 Drawing Sheets

OTHER PUBLICATIONS

Cassis et al., "Near-IR Imaging of Atheromas in Living Arterial Tissue" *Analytical Chemistry*, 65:1247-1256 (1993).

Jaross et al., "Determination of cholesterol in atherosclerotic plaques using near infrared diffuse reflection spectroscopy" *Atherosclerosis* 147:327-337(1999).

Cassis et al., "Cardiovascular Near-Infrared Imaging" http://www.pharm.uky.edu/ASRG/wave/cardiovascular_near-IR.html 9 pages, (2001).

Wang et al., "Near-infrared Spectroscopic Characterization of Human Advanced Atherosclerotic Plaques", *J. American College of Cardio.* 39:1305-13 (2002).

Moreno et al., "Detection of Lipid-Ricj Plaques With Near Infrared Spectroscopy In-Vivo" *Poster at American College of Cardiology conference*, Mar. 2001.(1 page).

V. Neumeister et al. "Determination of the cholesterol-collagen ratio arterial atherosclerotic plaques using near infrared spectroscopy as a possible measure of plaque stability" *Atherosclerosis* 165: 251-257 (2002)

* cited by examiner

NEAR-INFRARED SPECTROSCOPIC ANALYSIS OF BLOOD VESSEL WALLS

TECHNICAL FIELD

This invention relates to near-infrared spectroscopic examination of blood vessels to detect and characterize lesions such as atherosclerotic plaques.

BACKGROUND

Atherosclerosis is an arterial disorder involving the intima of medium- or large-sized arteries, including the aortic, carotid, coronary, and cerebral arteries. Atherosclerotic lesions or plaques contain a complex tissue matrix, including collagen, elastin, proteoglycans, and extracellular and intracellular lipids with foamy macrophages and smooth muscle cells. In addition, inflammatory cellular components (e.g., T lymphocytes, macrophages, and some basophils) can also be found in these plaques. Disruption or rupture of atherosclerotic plaques appears to be the major cause of heart attacks and strokes, because after the plaques rupture, local obstructive thromboses form within the blood vessels. Although the risk of plaque rupture usually cannot be predicted, many postmortem examinations have revealed that this risk depends mainly on plaque composition. Most ruptured atherosclerotic plaques are characterized structurally by the formation of a large, soft, lipid-rich, necrotic core covered by a thin fibrous cap, densely infiltrated by macrophages. Of these features, lipid accumulation in so-called "lipid pools" is the most frequently observed precondition for rupture. Inflammation is also a major feature of nonruptured, but eroded, thrombosed plaques.

Near infrared (NIR) spectroscopy has been used in industry for over 20 years for analysis of chemical materials either quantitatively or qualitatively. It has played a significant role in process and product control functions, because the spectra are not severely affected by atmospheric water or carbon dioxide. NIR spectra consist of overtones and combinations of fundamental IR bands, which can lower the resolution of the spectral features compared to other spectroscopic methods that have narrower bands, such as infrared (IR). However, new statistical techniques can be used to extract useful information from the lower resolution NIR spectral data. For example, chemometrics, which combines spectroscopy and mathematics, can provide clear qualitative as well as quantitative information. Thus, NIR spectroscopy combined with chemometrics has been used more frequently in a number of disciplines.

For example, NIR spectra have been obtained of biological tissue samples in vitro. In addition, some efforts have been made to image tissues in vivo; however, such imaging poses numerous challenges, including the problem of imaging though whole blood, which can mask and obscure spectral images of desired targets.

SUMMARY

The invention is based on the discovery that if one uses two or more single wavelengths and/or one or more narrow wavelength bands (covering, e.g., 2 to 10, 20, 30, or more nanometers up to about 100 mn) within a specific range of NIR wavelengths (1100 to 1415 nanometers), one can characterize vascular tissue, in vivo, e.g., through whole blood, to determine the composition of the tissue, e.g., the chemical composition, including the presence of lipid components, which can indicate whether a particular tissue is diseased or not diseased. In particular, one can characterize lesions of the tissue as "vulnerable," i.e., likely to rupture, and thus life-threatening, or "safe," and thus not life-threatening. Thus, the invention features methods of discriminating between diseased and healthy tissue in a blood vessel wall in vivo.

In general, the invention features methods of spectroscopically analyzing blood vessel walls in vivo using two or more single wavelengths or any one or more wavelength bands, each covering 1 to 10, 20, 30, or more nanometers of NIR radiation within a wavelength range of 1100 to 1415 nm, to illuminate the blood vessel walls. The use of these single wavelengths or narrow bands within this small wavelength range simplifies data acquisition and analysis, yet provides highly accurate and repeatable results. The vessel walls can be illuminated and the diffusely reflected light resulting from illumination of the walls can be analyzed either with blood in the vessel, or optionally with blood removed or replaced, e.g., temporarily, from the vessel.

Due to the nature of devices that generate light and radiation, illumination of a sample or target tissue with a "single wavelength" means illumination with a peak intensity at a specific wavelength, along with some illumination of the adjacent wavelengths.

The methods include illuminating the vessel wall and then collecting the radiation reflected via an optical fiber within a catheter then converting the reflectance intensities into absorbance intensities as a function of wavelength, and optionally pre-processing the spectra using techniques, such as mean centering (MC), autoscaling, normalization, first and second derivatives, smoothing options such as Savitzky Golay smoothing, varied baseline removal techniques, orthogonal signal correction, generalized least squares filtering, wavelets, standard normal variant (SNV) techniques, multiplicative scatter correction (MSC) techniques, and other techniques used to remove unwanted signals.

In general, the invention features an in vivo method for characterizing tissue in a blood vessel wall by (a) illuminating a tissue in the blood vessel wall with any two or more single wavelengths or one or more narrow wavelength bands of near-infrared radiation within a wavelength range of about 1100 to 1415 nm; (b) detecting radiation reflected from the tissue having a wavelength of from about 1100 to 1415 nm; (c) processing the detected radiation to characterize the tissue in the blood vessel wall; and (d) providing an output indicating the tissue characterization.

The invention also includes a method of analyzing tissue in blood vessel walls in vivo utilizing a fiber optic probe by introducing the probe into a blood vessel; directing onto the tissue in the blood vessel wall near-infrared radiation comprising any two or more single wavelengths or one or more narrow wavelength bands within a wavelength range of about 1100 to 1415 nm; detecting radiation within a wavelength range from substantially 1100 to 1415 nm not absorbed by the blood vessel wall; and analyzing the detected radiation to categorize the tissue in the blood vessel wall.

In all of these methods, the one or more narrow wavelength bands can each span about 1.0 nm to about 100 nm within the wavelength range of 1100 to 1415 nm. Alternatively, the method can use two single wavelengths, or two narrow wavelength bands, each spanning 1.0 nm to 30 nm within the wavelength range of 1100 to 1415 nm, or at least one narrow wavelength band and at least one single wavelength.

In these methods, the wavelength range can be about 1100 to 1350 nm, 1150 to 1250 nm, 1175 to 1280 nm, or about 1190 to 1250 nm. The blood vessel can be an artery, e.g., a coronary artery, and the tissue can include a lipid pool, a lipid pool and a thin fibrous cap, a lipid pool and a thick fibrous cap, and fibrotic and/or calcific tissue. The method can be used to illuminate tissue through blood, e.g., through 1, 2, 3 or more mm of blood.

In certain embodiments, the method can also include illuminating the tissue in the blood vessel wall with any two or more single wavelengths or one or more narrow wavelength bands of near-infrared radiation within a second wavelength range of about 1650 nm to 1780 nm; and further detecting radiation reflected from the tissue having a second wavelength of from about 1650 nm to 1780 nm. This second wavelength range can also be about 1650 to 1730 nm.

In all of these methods, the processing can be done using chemometric discrimination algorithms, and the methods can further include preprocessing the detected radiation to remove spectral information not related to a characterization of the tissue.

In another aspect, the invention also includes an apparatus for characterizing tissue in vivo that includes a near-infrared radiation source that generates radiation comprising any two or more single wavelengths or one or more narrow wavelength bands of near-infrared radiation within a wavelength range of about 1100 to 1415 nm, e.g., 1100 to 1350 or 1150 to 1250 nm; one or more radiation conduits for transmitting radiation from the radiation source to the tissue and for receiving radiation not absorbed by the tissue; a radiation detector that collects radiation not absorbed by the tissue across a wavelength range of substantially 1100 to 1415 nm; a processor that processes the collected radiation to characterize the tissue; and an output device that indicates the characterization of the tissue. For example, the near-infrared radiation source can generate two narrow wavelength bands, each spanning 1.0 nm to 30 nm within the wavelength range of 1100 to 1415 nm. The apparatus can further include a near-infrared radiation source that generates radiation comprising any two or more single wavelengths or one or more narrow wavelength bands of near-infrared radiation within a second wavelength range of about 1650 to 1780 nm. The source for the second wavelength range can be the same as or different from the source that generates the first wavelength range.

In another embodiment, the invention includes an instrument for characterizing portions of tissue in vivo that includes a) means for illuminating portions of tissue with near-infrared radiation comprising any two or more single wavelengths or one or more narrow wavelength bands of near-infrared radiation within a wavelength range of about 1100 to 1415 nm; b) means for collecting radiation within the wavelength range that is not absorbed by the tissue; c) means for determining from the collected radiation the amounts of absorbance of radiation by the illuminated tissue; and d) means for discriminating one illuminated tissue component from another illuminated tissue component within the wavelength range, wherein the discriminating means that include i) means for preprocessing the absorbance amounts using a chemometric preprocessing technique, and ii) means for performing a chemometric discrimination algorithm on the preprocessed absorbance amounts to characterize the tissues; and e) means for providing an output indicating the characterization of the illuminated tissue.

All of the methods herein can further include applying chemometric algorithms designed to characterize a lesion based on its tissue type or by the presence of specific chemical compositions. These algorithms can be developed to operate independently of blood depth, using spectra acquired at various blood depths, or developed using tissue type data and/or the presence of specific chemical compositions as determined by standard methods (e.g., pathology or chemical analysis).

In certain embodiments, the lesions are designated as falling within one of two categories: vulnerable (life-threatening) and safe (not life-threatening). One or more tissue types or specific chemical compositions may fall within each category. For example, a lesion with high lipid content and a thin fibrous cap is considered a "vulnerable" plaque, one which is life threatening. Lesions that mainly contain fibrous, calcific, and/or have a high lipid content, but with a thick fibrous cap, as well as normal or pre-atheroma tissue, are characterized as "safe."

In another embodiment, the lesion is continuously graded by the output of the algorithm as to its "vulnerability potential" where a stable, safe lesion may be arbitrarily designated a low risk index (e.g. <1.0) and a plaque that is of very high risk is assigned a high risk index (e.g. 10).

In other embodiments, the lesions are designated as falling within one of three categories: vulnerable (high lipid content, thin cap), potentially vulnerable (i.e., monitor the lesion over time; high lipid, thick cap), and safe (fibrous, calcific, normal, or pre-atheroma). In other embodiments, the lesions are designated as falling within one of five categories: lipid-containing tissue with a thin fibrous cap, lipid-containing tissue with a thick fibrous cap, fibrous tissue, largely calcific tissue, and normal or pre-atheroma tissue. These different categories can be used to provide additional diagnostic and prognostic information as compared to the methods in which only two or three categories are provided. In this, and other embodiments, the chemometric algorithm can be based on the presence of other chemical compositions relating the lipid pool and thin cap, along with other markers, to an index of vulnerability by developing algorithms using spectra acquired from various tissue types or chemical compositions which are known by standard methods (e.g., pathology or chemical analysis) as part of the discrimination method.

In other embodiments, the chemometric algorithm is applied to classify spectral measurements into one of two or more depth classes (e.g., 0 to 1.5 mm and 1.5 mm and above away from the tissue). In this, and other embodiments, the chemometric algorithm can be based on the depth classification, both in the presence of or without blood, and can be applied to discriminate tissue types or the presence of chemical compositions, or the algorithm can be developed using spectra acquired at various depths, and using tissue types or chemical compositions which are known by standard methods (e.g., pathology or chemical analysis) as part of the discrimination method.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 4B is a plot of the data shown in 4A, only the data have been offset by the absorbance at 1125 nm for each spectrum.

DETAILED DESCRIPTION

General Methodology

Figure 1:
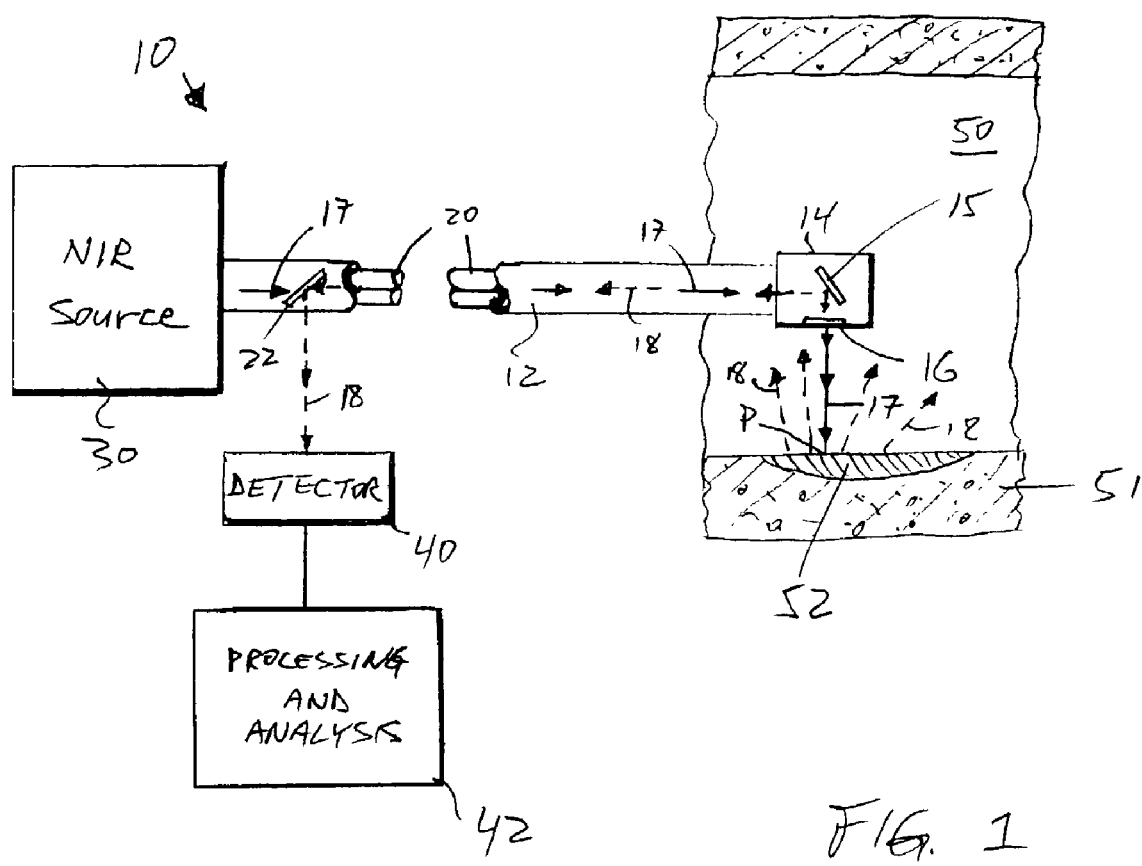
FIG. 1 is a schematic diagram of an imaging system for spectroscopically analyzing blood vessel walls using the new methods. Either a single fiber may be used for both delivery and detection of light or multiple illumination-detection fiber channels can be employed.

In general, the invention features methods of using any two or more single wavelengths or one or more narrow wavelength bands, each covering 1 to 10, 20, 30, 40, 50, 60, even 100 or more nm, of NIR radiation within the wavelength range of 1100 to 1415 nm (e.g., 1100 to 1350 nm, 1100 to 1300 nm, 1150 to 1255 nm, 1200 to 1250 nm, or 1175 to 1225 nm) to illuminate blood vessel walls in vivo, with or without the presence of blood. Data obtained within these wavelengths enable the operator to distinguish between diseased and healthy tissue located within a blood vessel wall.

The single wavelengths can be used in pairs or in combinations of multiple single discontinuous wavelengths, or in conjunction with one or more of the narrow wavelength bands. The wavelength bands can be used individually, in pairs, or other multiples and with the same or different band widths. For example, one can use a 10, 20, or 30 nm band, e.g., from the 1190 to 1220 nm region, and combine it with a band from the 1220 to 1250 nm region, as the incident NIR radiation to illuminate blood vessel walls in vivo.

More specifically, by obtaining data at two or more single wavelengths, e.g., at 1190 and 1250 nm, or from one or more narrow wavelength bands, or a combination of single wavelengths with narrow band regions (e.g., 1190 to 1250 nm, or 1145 to 1175 nm with 1250 to 1280 nm or 1175 to 1205 nm with 1310 to 1340 nm) one can get sufficient information to make a clear diagnosis of any lesion, such as an atherosclerotic plaque, in a blood vessel wall as either vulnerable or safe. Of course, larger regions, such as the full 1100 to 1415 nm range, 1150 to 1350 or 1250 nm, 1175 to 1250 nm, 1100 to 1200 nm, 1200 to 1300 nm, 1250 to 1350 nm, 1215 to 1285 nm, and the like also work, and provide even more information, but at the cost of added computational complexity.

The narrow bands or regions covering 2, 5, 10, 20, 30, 40, up to 100 or more nm, can also be used in pairs or triplets (or more), as long as at least one band region is within the overall range of 1100 to 1415 nm. Thus, for example, illumination in the 1100 to 1415 nm wavelength range can be combined with illumination in the about 1560 to 1780 nm range (e.g., 1600 to 1780, 1600 to 1700 nm, or 1650 to 1745 or 1730 nm).

If more than one band is used, the pairs or triplets can be, but need not be, contiguous. For example, one can use a 30 nm band from 1190 to 1220 nm, and a second band from 1220 to 1250 nm as the incident NIR radiation to illuminate blood vessel walls in vivo. Alternatively, one can use a band that covers from 1145 to 1175 nm and another band that covers from 1250 to 1280 nm. One can also use a narrow band that covers from 1175 to 1205 nm and a band that covers from 1310 to 1340 nm. Other pairs, triplets, or multiplets of bands or single intensities can be used. In addition, the pairs, triplets, or multiplets of bands can be of different sizes, e.g., a pair of bands where one covers a band of 20 nm and the other covers 40 nm, or the same size, e.g., a pair in which both bands cover 30 nm. Other examples and combinations are possible. For example, one can use a single wavelength and a narrow band, or two single wavelengths, or two single wavelengths and two different bands. One can also use three, four, or more single wavelengths within the 1100 to 1350 range.

One important aspect of the 1100 to 1350 range of wavelengths is that it allows one to obtain relevant spectral data from blood vessel walls in vivo through blood (and independent of the distance from the illumination tip to the vessel wall), which can otherwise interfere with accurate readings at other wavelengths. This spectral data enables accurate characterization of the vessel wall in vivo as diseased or not diseased tissue. Not only does this wavelength range enable collection of data relevant to detecting lesions, such as atherosclerotic plaques, through blood within a living subject, such as a human or animal, it permits the operator to characterize the lesion, i.e., to determine whether a detected plaque is "vulnerable," i.e., likely to rupture, or "safe," i.e., unlikely to rupture. More specific characterization is also possible.

The spectra received from the blood vessel walls are analyzed by taking single point readings and determining whether the location of the vessel wall corresponding to that point reading is predominantly lipid with a thin cap (vulnerable or "life-threatening"), lipid with a thick fibrous cap (potentially vulnerable), or predominantly non-lipid, normal, fibrotic, or calcific (safe or "non-life threatening"). Thus, the operator can create two (vulnerable/diseased or safe/healthy), three (vulnerable (diseased), potentially vulnerable (diseased), or safe (healthy)), or more different categories for lesion types as described further herein.

The new methods of analyzing tissue in vivo broadly include the steps of directing NIR radiation onto the tissue to be analyzed (though blood or without blood) and then detecting the resultant radiation, converting the reflected signal to absorption values, optionally preprocessing the returned signal, and processing the NIR radiation reflected by the tissue. The tissue lesions can be located in any blood vessel, including the aorta and arteries such as the coronary, carotid, femoral, renal, and iliac arteries. As indicated above, the incident NIR radiation directed onto the blood vessel walls is any two or more single wavelengths or any one or more narrow bands within the wavelength range from 1100 to 1415 nm. To obtain the spectrum, the incident NIR radiation must be directed onto the blood vessels walls, and the spectrum must be collected from the blood vessel walls. These steps are carried out using a fiber optic probe or catheter that is introduced into the blood vessel in a subject, such as a human or animal, e.g., a domestic animal such as mammals, e.g., dogs, cats, horses, pigs, cows, rabbits, mice, hamsters, government officials, and the like. The new methods can also be carried out on non-human primates, such as monkeys, but are typically used for human patients.

The spectrum can be collected using the same fiber optic cable or another channel separate from the illumination fiber optic cable, which can be in the form of a catheter or probe that delivers the reflectance illumination from a single light source as seen in FIG. 1. The detector converts the collected NIR radiation into an electrical signal, which can be subsequently processed using signal processing techniques. Alternatively, multiple illuminators and detectors can be used within the fiber optic system, using a single or multiple fiber assembly for both illumination and collection of the NIR radiation.

The methods further include the steps of analyzing the electrical signal corresponding to the reflectance spectra, and producing graphical or other representations thereof. The electrical signal may be converted to digital data. Advantageously, all of the steps provide high-speed data acquisition and analysis, because only single wavelengths or narrow bands of wavelengths are used in the new methods. Such steps can be performed using, for example, a processing chip, DSP, EPROM, etc., such as those found in personal computers, and an appropriate algorithm, e.g., a chemometric algorithm, which can be embodied in the processing software or processing hardware. Based on this analysis, vascular tissue can be characterized as to its composition, or as to whether it is diseased or not diseased. For example, the vessel wall may be characterized as to whether it is high in lipid content, fibrous content, and/or calcific content. These parameters enable the user to categorize the lesion as either vulnerable (diseased or life-threatening) or safe (healthy or non-life-threatening). In other embodiments, the lesions can be characterized as vulnerable (lipid-containing tissue with a thin fibrous cap (diseased)), potentially vulnerable (lipid-containing tissue with a thick fibrous cap (diseased)), or safe (fibrous or calcific tissue, (but still diseased)). The "diseased" categories can be separated as well to provide diseased categories or classifications, and a normal (healthy) category for a blood vessel wall without any lesions.

Once a lesion or plaque is detected and determined to be vulnerable (or diseased), various technologies can be used for removing or stabilizing the plaque before it ruptures. For example, lasers can be used to ablate the plaque (see, e.g., Leon et al., J. Am. Coll. Radiol., 12:94-102, 1988; Gaffney et al., Lasers Surg. Med., 9:215-228, 1989). Alternatively, one can use brachytherapy, angioplasty, stenting (coated or not), and photodynamic therapy.

Preprocessing of Data

Figure 2:
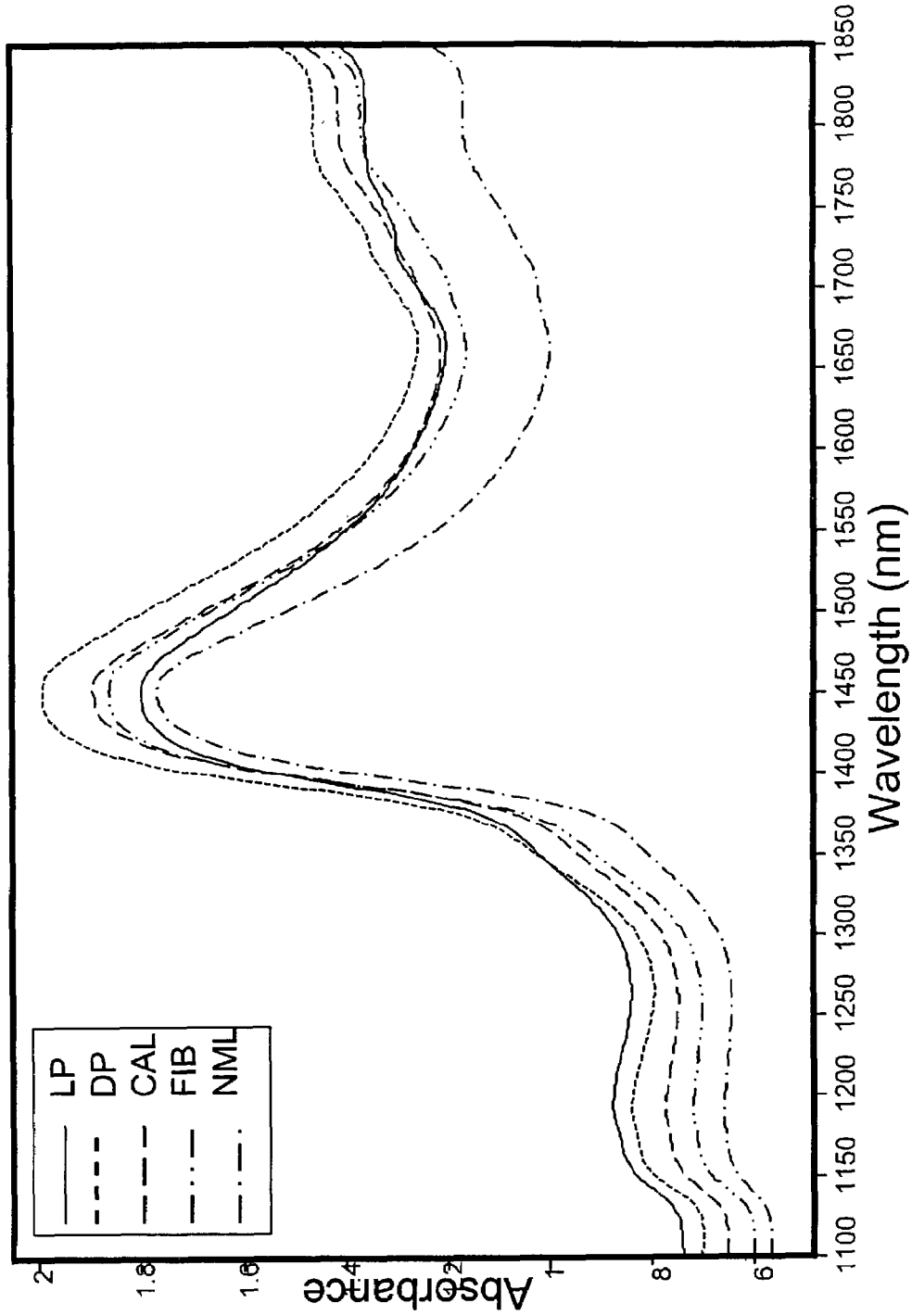
FIG. 2 is a plot of NIR absorbance versus wavelength for various human aorta samples resulting from illumination of the tissue with NIR radiation within the wavelength range of 1100 to 1850 nm. Spectra for calcific, fibrotic, lipid-containing, and normal tissues are shown.
Figure 3:
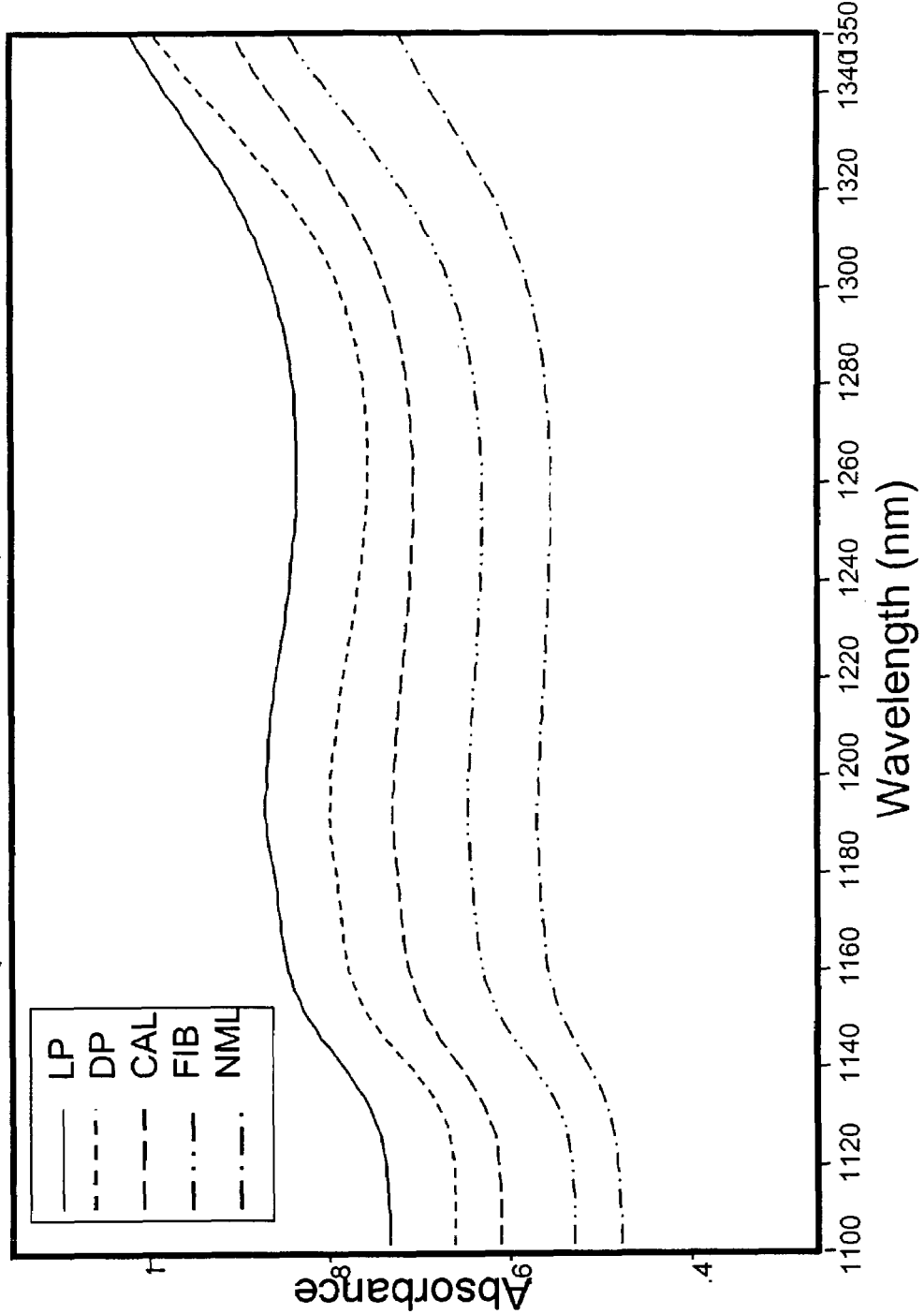
FIG. 3 is a plot of NIR absorbance versus wavelength for various human aorta samples resulting from illumination of the tissue with NIR radiation within the wavelength range of 1100 to 1350 nm. Spectra for calcific, fibrotic, disrupted plaques, lipid-containing, and normal tissues are shown.
Figures 4A, 4B:
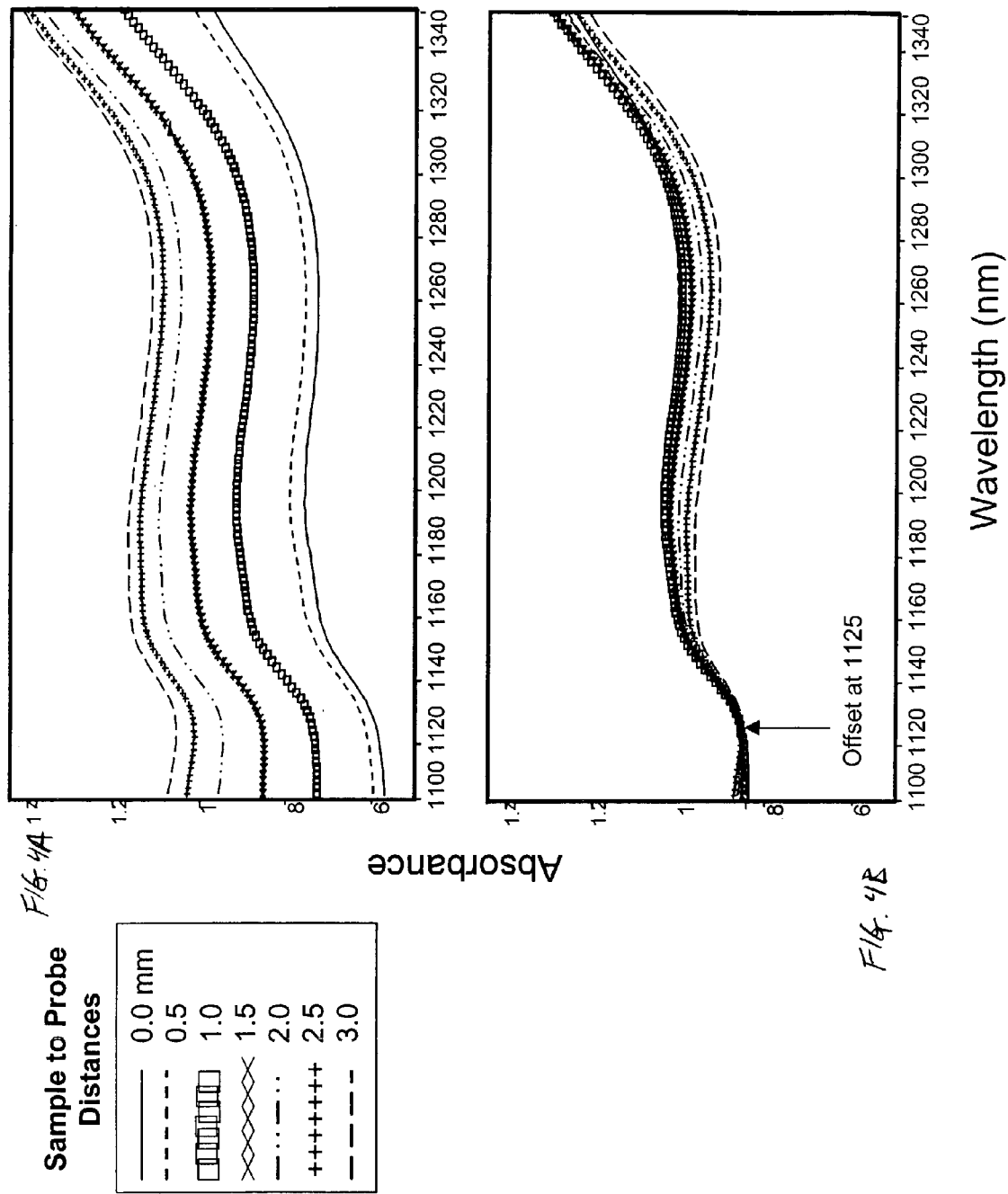
FIGS. 4A and 4B are plots of diseased tissue samples as a function of distance from the top of the tissue to the base of the fiber optic probe spanning eight different tissue-to-probe separations from 0.0 mm to 3.0 mm with blood intervening.

The digital data may be first preprocessed to remove interferants unrelated to the signal of interest, such as the baseline slope, the offset, and/or the linear or multiplicative effects of scattering. The spectral data can also be centered with respect to each other, autoscaled, normalized, etc. to enhance the small spectral features pertaining to the component of interest The benefits of preprocessing are demonstrated in an experiment in which spectra were obtained through bovine blood of four tissue types found in atheromatous human aortas. The absorbance versus wavelength spectra are shown in FIG. 2 from 1100 nm to 1850 nm. Three disease states are represented as a composition of mainly lipid pool, fibrotic, or calcific, with one spectrum of the normal tissue. These diseased states were determined using the histology and pathology analysis and then categorized and separated by the amount of each composition contained in that particular diseased plaque. FIG. 3 shows similar spectra within the smaller wavelength range of 1100 to 14150 nm. Five categories are shown, including calcific, fibrotic, disrupted plaque, lipid-containing, and normal. FIGS. 4A and 4B show spectra of a diseased tissue sample viewed through various depths of sample to probe separations with bovine blood intervening. Plot 4B has been adjusted by removing the offset at 1125 nm from each of the spectra to remove the major differences due to the sample to probe separation. Measurements were made at 0.0, 0.25, 0.5, 1.0, 1.5, 2.0, 2.5 and 3.0 mm from the tissue surface. As the probe moves further away from the tissue surface, the features seen when the probe was pressed against the tissue become much weaker.

The absorbance can be used directly, but as can be seen from FIGS. 2 and 3, there are offsets and slopes that in general confound the information coming from the absorbance related to the chemical composition or tissue type. There are a number of ways to preprocess the spectra to remove these unwanted effects of shifted baselines and slopes from both the instrument and the biological system effects, along with those of scattering from the biological. Such methods include, but are not restricted to, first or second derivatives, normalization, autoscaling, multiple forms of baseline removal, mean centering (MC), multiplicative scatter correction, standard normal variant (SNV), Savitsky Golay smoothing, detrending, OSC, GLS filtering, wavelet filtering, FIR filtering, and combinations thereof, but not limited to these options. The spectra can be untreated, using the raw absorbance measurements, or they can be pre-processed before further data manipulation within the model building application. In one embodiment, the preprocessing option is standard normal variant combined with mean centering. In other embodiments, the preprocessing option is SNV with MC and detrending, or the spectra are pretreated by removal of the central mean (MC-mean centering). In another embodiment, the preprocessing is a Savistsky-Golay smoothing first derivative.

Figure 5:
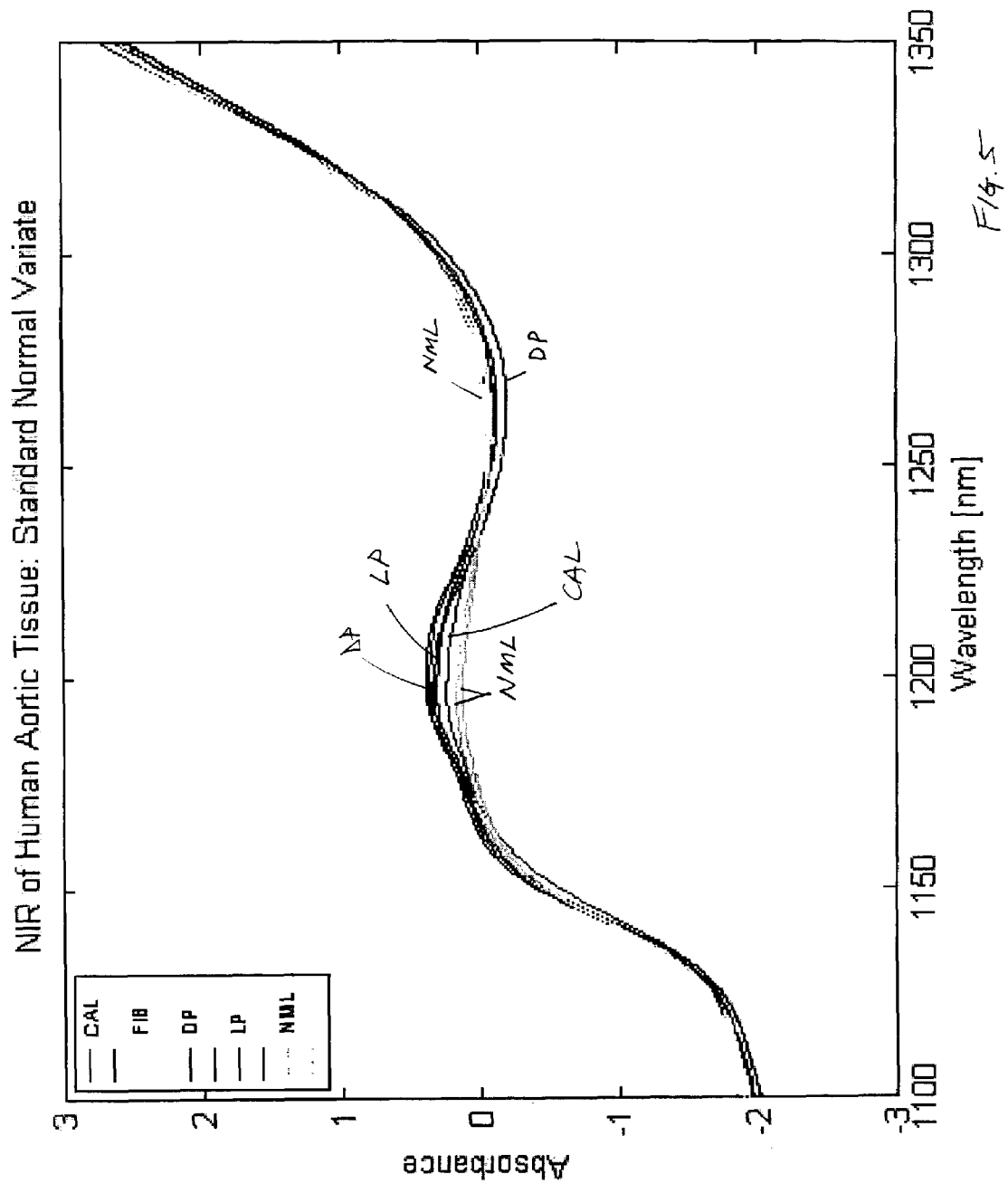
FIG. 5 is a plot of NIR absorbance versus wavelength for the same human aortic tissue samples as those displayed in FIG. 3, but after processing with a standard normal variant (SNV) technique. As shown, the spectra for calcific, fibrotic, disrupted plaque, lipid-containing tissues, and normal tissues, tend to overlap after SNV processing which removed the scattering differences of the samples.
Figure 6:
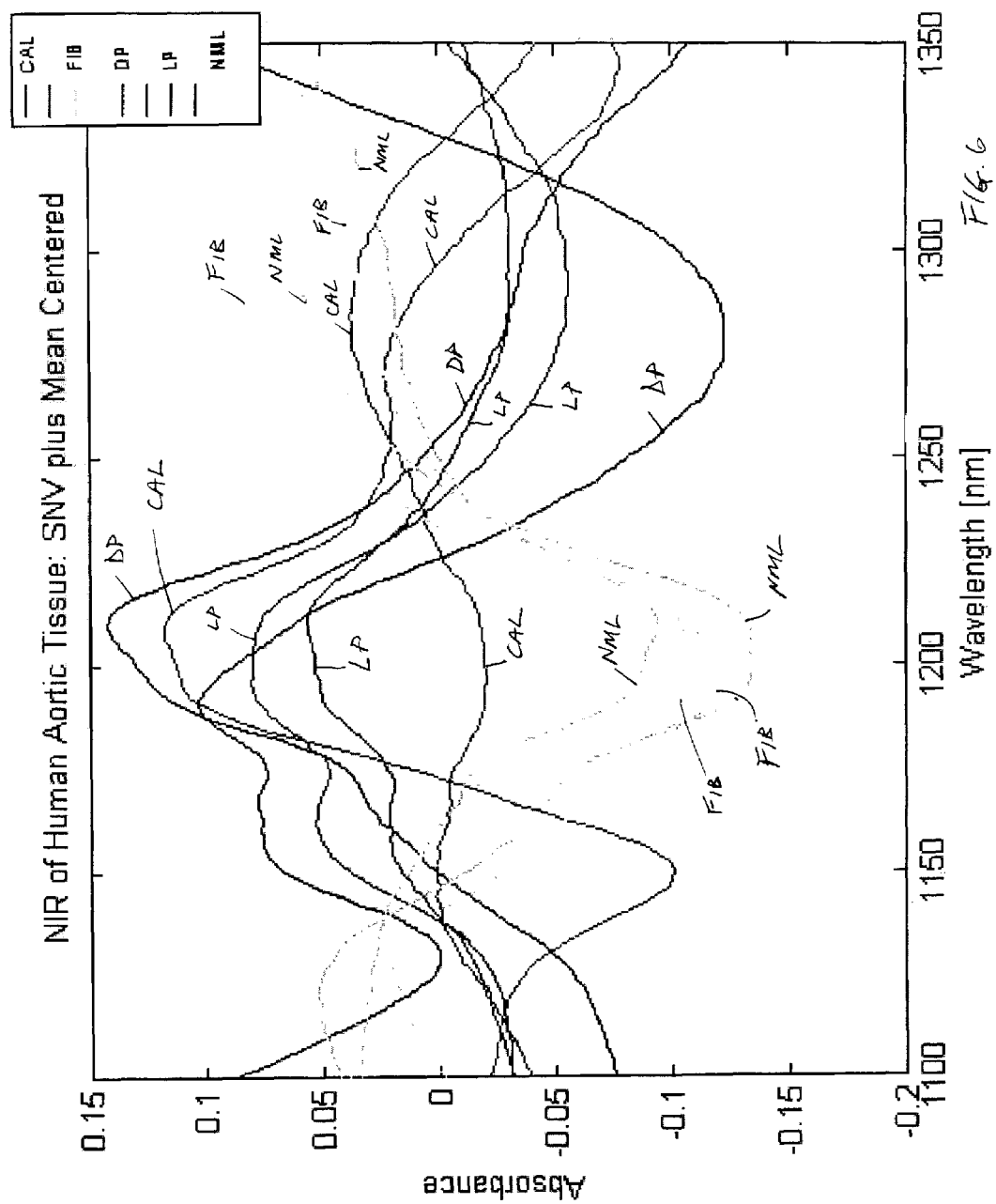
FIG. 6 is a plot of NIR absorbance versus wavelength for the same human aortic tissue after processing with a standard normal variant (SNV) technique as seen in FIG. 5, but the whole group of spectra was further processed by the addition of a mean centering (MC) technique which provides a global mean for all the spectra used to build the model. These techniques when combined indicate where the areas of greatest influence are within the spectral information.

For example, spectra of the specimens shown in FIG. 3 were preprocessed using standard normal variant (SNV) preprocessing. The results are shown in FIG. 5, which clearly demonstrates the successful use of a preprocessing option to remove the scatter between the different diseased tissue spectra, which can otherwise interfere with the process analysis. To further enhance the information contained within the preprocessed spectra, one can use additional techniques. For example, FIG. 6 shows spectra preprocessed with both SNV and mean centering (MC). Comparing FIG. 5 to FIG. 6, it is clear that there are a number of areas within the spectra that vary greatly with the additional preprocessing treatment of MC added to SNV. However, the regions in the spectrum that correspond to the chemical composition of interest within the lesion (in this case lipid pool concentration) are not easily obtained by merely observing the results of the preprocessed data. Thus, the preprocessed digital data is typically processed further to obtain a correlation between the data and the actual constituents within a blood vessel wall, i.e., to determine whether a lesion is vulnerable or safe.

Processing Data

The digital data can be further processed using any or a variety of discrimination algorithms to determine the nature of the correlation between the constituents within the blood vessel walls (as determined by an external means such as morphometry measurements or chemical analysis) and the spectral features obtained in the NIR spectrum (the digital data). Useful discrimination algorithms use computerized mathematical models developed by modeling the relationship between spectra and tissue states of known tissue samples. These models are typically based on large amounts of patient data or ex vivo data simulating in vivo data. The mathematical models can be based upon chemometric techniques such as Partial Least Squares Discrimination Analysis (PLS-DA), Principle Component Analysis with Mahalanobis Distance and augmented Residuals (PCA/MDR), and others such as PCA with K-nearest neighbor, PCA with Euclidean Distance, SIMCA, the bootstrap error-adjusted single-sample technique (BEST), neural networks and support vector machines, and other types of discrimination means.

The discrimination algorithm is applied to the digital data from the spectra of an unknown tissue sample in a blood vessel wall to categorize a particular location or point within the tissue. For example, the tissue can be characterized as being part of a lesion or plaque, and if so, whether this is a vulnerable or safe plaque as described above. An output, such as a audible or visual representation, e.g., a graph or other output, can be provided to indicate to the operator the characterization of the vascular tissue, including whether the illuminated blood vessel wall includes a plaque, and if so, whether the plaque is vulnerable or safe, or falls within one of the other categories described above or simply whether the site of illumination contains a plaque that is vulnerable.

Many different types of discrimination algorithms can be used, from the basic form of a simple absorbance comparison between two or more wavelengths, or analysis of large data matrices (raw or preprocessed) with techniques based upon multiple linear regression, Principal Component Analysis (PCA) as described by Malinowski et al, in "Factor Analysis in Chemistry" John Wiley & Sons, New York, 1980. These methods are used to obtain a metric to determine the nature of the diseased tissue from which the groups can be separated.

Figure 7:
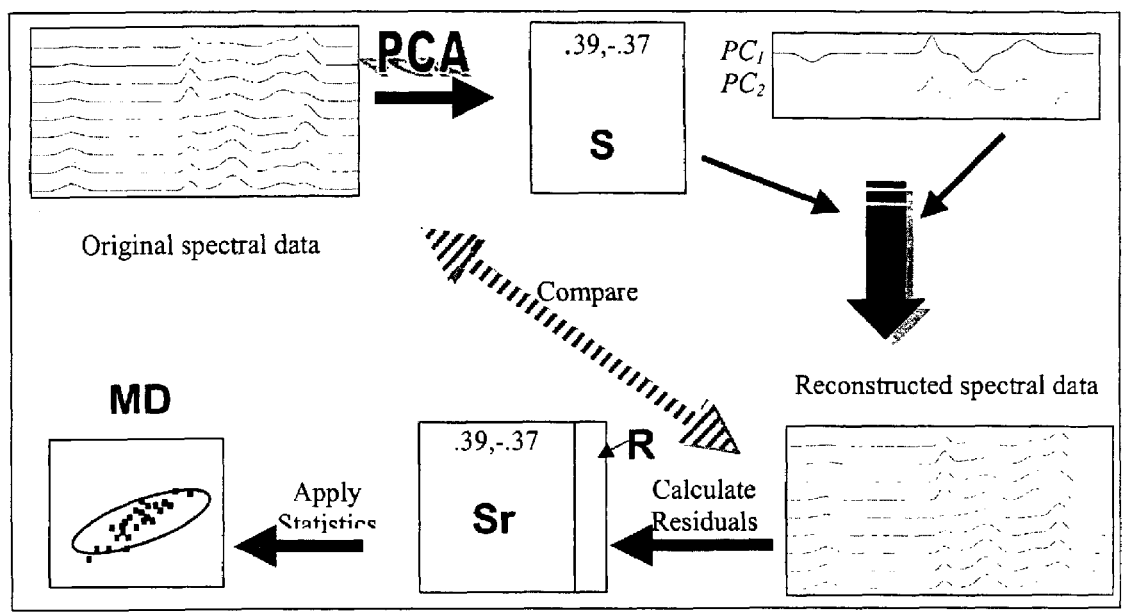
FIG. 7 is a schematic of a processing technique combining principal component analysis (PCA), a spectral decomposition method which breaks the original data into two matrices that contain the Principal Component (PC) vectors and the resultants scalars or Scores (S), coupled with the addition of the spectral residuals (R) to create an appended Scores matrix called Sr, and then applying the non-linear statistics of the Mahalanobis Distance (MD) calculations to the appended Scores (Sr) resulting in a discrimination method termed PCA/MDR.

For example, one embodiment uses PCA, which enables the use of large amounts of spectral data information, which can be decomposed (and therefore compressed) into a matrix of factors (or vectors, principle components, latent variables, eigenvectors, etc.) that retain only the largest variations expressed by all the spectra of the tissue type of interest, and a matrix of the resultant scores (or scalars, eigenvalues, etc.) used to scale the amplitude of each of the factor vectors. The upper half of FIG. 7 is a schematic that depicts the PCA process of spectral decomposition of the original spectrum into the Scores (S) and Principal Component (PC) matrices. As shown in the lower half of FIG. 7, the results are then analyzed by reconstructing the spectra from the combination of the S and PC values and then minimize the difference between the comparison of the original to the reconstructed spectra using the residuals (left over values from the comparison squared and then summed).

Once a metric has been chosen (in the case of PCA it is the resultant scores), a threshold is applied to determine the likelihood of whether the unknown tissue spectrum can be classified as the diseased tissue type or not. Many methods can be used for this determination such as a simple wavelength comparison technique using linear regression lines, or more complex geometries such as Euclidean or Mahalanobis distances as thresholds for more complicated separations. When analyzing large volumes of spectral data, PCA can be used and can also be combined with a variety of metrics for discrimination such as a linear regression line, e.g., such as the one used in the partial least squares-discriminate analysis (PLS-DA) method described in Ericsson et al., "Multi- and Megavariate Data) Analysis: Principles and Applications" (Umetrics Academy, 2001), Euclidean distance, and Mahalanobis distance as described by Marks et al in the following articles: Analytical Chemistry, 57, 1449, (1985); Analytical Chemistry, 58, 379, (1985) and Analytical Chemistry, 59, 790, (1987). Other elements besides the scores of the PCA decomposition can be used for a metric with a threshold, such as the soft independent modeling of class analogies (SIMCA) described in Gemperline et al., *Anal. Chem.*, 61:138, (1989), the bootstrap error-adjusted single-sample technique (BEST) described in Lodder et al., *Appl. Spec.*, 42:1352, (1988), and other discriminatory techniques which use the residual rather than the scores from the reconstructed spectra.

One embodiment combines PCA scores analysis using a linear threshold determined by minimizing the classification between two or more groups to establish the boundary calculations termed the PLS-DA method.

Another embodiment of the model algorithm is a variation of PCA combined with statistics of Mahalanobis Distance (MD) and the addition of the spectral residuals (R) described in a similar method developed by Gemperline et al., *Anal. Chem.*, 62:465, (1990) (see FIG. 7) where they combined PCA with SIMCA. This model embodiment, (PCA/MDR), developed by Duckworth, et al. of Galactic Industries and incorporated into their PLSplus/IQ™ Chemometric software uses PCA, SIMCA, and Mahalanobis Distances to determine the maximum discrimination of the model. This model is formed by calculating the Mahalanobis distance threshold on the matrix of the PCA score values from the spectral decomposition augmented with the mean centered sum squared residuals left over from the comparison of the reconstructed spectra to the original spectra used in the model. This matrix is termed (Sr) in FIG. 7 and contains the scores for the description of the maximum variation of the spectra contained in the model augmented with the mean centered summed squared residuals left over from the PCA decomposition. These values are then subjected to the Mahalanobis Distance calculations using the following equation:

$$M = \frac{(Sr)^T (Sr)}{(n-1)}$$

in which M is the Mahalanobis matrix, T indicates the transpose is taken of the Sr matrix, and normalized by n, the total number of spectra that were used to build the model. The Mahalanobis matrix is then used to calculate the Mahalanobis Distance (D) for each Score (i) produced in the model.

$$D_i = \sqrt{(Sr_i) M^{-1} (Sr_i)^T}$$

To make a comparison between all the members of the model, a root mean squared group (RMSG) size is then calculated for the model. This is done by obtaining the sum of all the squares of the predicted distances for each of the samples used in the model ($D_i$) normalized by the number of samples used in the model (n):

$$RMSG = \sqrt{\frac{\sum_{i=1}^{n} D_i^2}{(n-1)}}$$

The final calculation normalizes each of the Mahalanobis Distance ($D_i$) scores by the group normalization factor (RMSG). To determine whether the normalized score values are within the model group or outside of the model group values a boundary is set and in general this boundary is set at 3 standard deviations away. The Mahalanobis Distance is the first metric used to determine if an unknown sample is part of the model group or not.

The final decision as to whether a spectrum from an unknown tissue sample fits the particular model can be made using three metrics: (i) the fit of the unknown residual augmented scores to the Mahalanobis Distance based upon the residual augmented scores of the model, (ii) the resultant residual of the unknown spectrum compared to a distribution test such as a T-test or F-Test of the model residuals, and (iii) a comparison as to whether the unknown score fits within the range of scores used to build the model.

To determine if the unknown sample is part of a specific group or category, the spectrum of the unknown is first preprocessed in the same manner as the model and then decomposed into its PCA components plus residual. The mean residual value obtained from the model is then subtracted from the unknown residual to obtain the Sri value, where (i) represents the residual augmented scores vector for each of the individual unknowns. This value is then applied to the following equation to obtain the square of the Mahalanobis Distance (D) for each of the (i) unknowns:

$$D_i = \sqrt{(Sr_i) M^{-1} (Sr_i)^T}$$

This distance is then divided by the group RMSG value before testing the calculated Mahalanobis Distance of the unknown against the standard deviation of the all the distances obtained from the model. In one embodiment, three standard deviations (3σ) are used for the Mahalanobis Distance boundary of the model. This is the first of three "flags" or indicators used as a disease index to ascertain whether the unknown sample falls within the model group (category) or not. The second flag is obtained from the model residuals. A standard distribution test such as a T-test, Chi-Squared, or F-Test is then applied to the model residuals at some level such as the 99% level, and this value is used to determine if future predicted residuals fall within the model range. The third flag is the comparison of the unknown score to the maximum and minimum score of the model or compared to a standard distribution test such as the T-test, Chi-Squared, or F-Test performed at some level such as the 99% level. If any one of the three flags is not present (false), then the sample is ruled not to fall within the model group/category being tested.

Devices for Use in the New Methods

To perform the new methods, an improved apparatus is provided for analyzing lesions and plaques in blood vessel walls in vivo. The apparatus can also be used for in vitro analysis. The new apparatus includes an external radiation source, such as a laser or other NIR radiation source for transmitting the incident NIR radiation within the wavelength range of 1100 to 1350 nm and at sufficient power. This source can provide the desired NIR radiation region by scanning or by generating NIR radiation that spans the wavelength bands described herein. In addition, the source can provide two or more single wavelengths within this range similar to filter based NIR instruments. The radiation can be delivered sequentially or simultaneously. A variety of NIR sources can be used to provide the required incident NIR radiation. For example, NIR spectra can be obtained from human blood vessels, such as the coronary arteries or aorta, using light sources such as tunable semiconductor lasers or solid-state lasers, fiber-coupled systems such as Raman amplifier lasers, or super continuum fiber lasers and other light sources such that the wavelengths can be scanned. Alternatively, the light source may produce spectral bands that enable simultaneous illumination of the specimen with all required wavelengths. Tuning and/or spectral detection must occur rapidly (<1 second) to avoid motion artifacts within the arteries. Monochromatic fixed-wavelength sources such as lasers, LED's, semiconductor diode lasers, DFB, can also be multiplexed to serve as the illumination source for spectroscopic measurement.

Radiation is carried from the NIR source to the blood vessel walls via any of a number of types of fiber optic catheters or probes operatively connected to the NIR radiation source (see, e.g., Tearney et al., U.S. Pat. No. 6,134,003; Crowley et al. (BSC), U.S. Pat. No. 5,588,432; and Colston, et al, U.S. Pat. No. 6,175,669. For example, the catheter can have a single fiber optic core. A radiation directing or focusing mechanism can be mounted to the distal end of the catheter to enable the operator to direct or focus the NIR radiation onto a desired target on a blood vessel wall. The focusing mechanism should be adapted to compress the incident radiation beam from the transmitting catheter onto a small spot on the tissue surface to be analyzed. NIR radiation reflected by the tissue of the blood vessel wall can be directed into a receiving optic fiber or fibers to provide a convenient, cost-effective means for directing the light reflected from the specimen to the spectroscopic measurement device. Additionally, the apparatus includes one or more detectors present at the distal portion of the catheter for rapidly detecting the radiation reflected or scattered back from the blood vessel wall being illuminated.

FIG. 1 illustrates one of several embodiments of an apparatus 10 that can be used to carry out the present invention. Depending upon the specific wavelengths used, the apparatus is optimized in a manner to enhance the performance within those bands. This includes, but is not restricted to, optimizing the optical fiber cutoff range, the reflectivity of director (mirror) substrate, the addition of lenses, the material and other properties of the sheath, and other apparatus items that can be changed to optimize the signal received. More particularly, the apparatus 10 includes a fiber optic probe or catheter, generally designated by reference numeral 12. The catheter 12 has a distal end 14. The distal end 14 of the catheter can also include an optical aperture 16 through which NIR radiation is directed and/or focused (via redirecting and focusing means 15). This aperture can be centrally located or directed to one side of the distal end (as shown).

An optical fiber or fiber optic bundle 20 is located within catheter 12. The fiber optic bundle 20 is operatively connected to a NIR radiation source 30 and detector source 40 (see FIG. 1). The NIR source 30 is particularly adapted for generating multiple (e.g., 2, 3, 4, or more) single wavelengths or a wavelength band of any 1, 2, 5, 10, 15, 20, 30, 40 or more nm within the overall wavelength range of from 1100 to 1415 nm.

An individual NIR radiation detector 40 includes one or more detectors present at the distal portion of the catheter, such as lead sulfide detectors, InGaAs, Silicon, Ge, GaAs, indium antimonide detector cooled with liquid nitrogen, e.g., singly or in an array, for rapidly detecting the radiation reflected or scattered back from the blood vessel wall being illuminated. Catheter 12 is inserted into the patient via a peripheral vessel and moved to the desired target 52 area (lesion) using standard techniques and methods. Then, NIR radiation within the 1100 to 1415 nm wavelength range from source 30 is directed along the transmitting fiber optic bundle 20 to the fiber optic catheter 12. There, the NIR radiation from source 30 is projected as an incident beam 17 through the optical aperture 16 onto a blood vessel wall 51 (incident light beam is depicted in full line arrows).

A significant portion of the incident NIR radiation is projected onto point P of the blood vessel wall 51. The same catheter or probe that illuminates the blood vessel walls is typically also used to collect radiation reflected from the target (the so-called "reflectance spectrum"). For example, as shown in FIG. 1, radiation is reflected back into catheter 12 through aperture 16. The scattered, reflected radiation is shown at dash line arrows 18. Catheter 12 directs the reflected radiation so that it falls upon detector 40 via the radiation redirecting and focusing means 15 and a beam splitter 22.

This reflected spectral information must be processed to obtain useful information. As shown in FIG. 1, detector 40 is connected to a means 42 for preprocessing, processing, and analyzing the detected spectra and producing the analyzed results as a functional color scheme or other method to indicate whether the lesion is included or excluded from the model thereof. Specifically, the analysis is completed over selected wavelength region or regions of the incident NIR radiation directed upon the tissue. Thus, reflected radiation within the wavelength range from 1100 to 1415 nm is analyzed or the 1100 to 1415 nm radiation coupled with radiation in the 1650 to 1780 nm region is analyzed. To achieve this end a computer can be used that includes appropriate analytical algorithms as discussed herein.

Experimental Models

The new methods are based upon studies in which NIR spectroscopy was used to examine human aortic samples through whole blood. The samples contained both normal and diseased tissue pertaining to various stages of atherosclerotic plaque growth. The resulting reflectance spectra were converted to absorbance spectra as a function of the log of 1/Reflectance and were analyzed using chemometric techniques that provide a means for modeling the data in such a manner to maximize the spectral information pertaining to the lipid pool content as obtained through blood. Thus, the determination of plaque vulnerability is based, at least in part, on the nature of the lipid pools within atherosclerotic plaques, and their spectral patterns when covered by thicker or thinner fibrous caps.

Computer modeling identified the NIR wavelength range from 1100 to 1415 nm as unique for use in predicting the nature of the lipid pool content in human atherosclerotic plaques. In addition, it was determined that sufficient information could be obtained by illuminating the target tissue with two or more single wavelengths, multiple combinations of single wavelengths or one or more narrow bands of wavelengths, each covering as few as 1, 2, 4, 10, 15, 20 or 30 nm (or up to 100 nm or more), within this range of 1100 to 1415 nm or with a combination of the 1100 to 1415 nm range with the about 1600 to 1780 nm range.

Two chemometric discriminant techniques were used in this study, PCA/MDR and PLS-DA, both based upon PCA, but there are many other discrimination methods that can be used to build the prediction models such as those described above. As discussed above, PCA is a linear regression method that decomposes the spectral information into a smaller set of vectors (principal components, factors, eigenvectors, latent variables, etc.) and scalars (scores, eigenvalues, etc) that describe the variations of the spectral components while leaving out random noise components. Both methods require a training set of representative samples, but differ in the assembly and treatment of those samples. The training set is used to build a mathematical relationship that recognizes similar qualities for a single (or more) classification group, and then the model acts as a screening tool for all subsequent samples tested. The segmentation into the various classification groups was based upon the morphology and morphometry results of the tissue samples. Both discrimination methods are based upon the ability of the samples containing mainly lipid pool (LP) to be distinguished from a combined set of mainly fibrotic tissue (FIB) and calcific tissue (CAL) specimens, and also from normal tissue (NML) through blood.

In the first case, PCA/MDR, the PCA scores from the LP specimen spectra are combined with the remaining noise components (residuals) and a Mahalanobis Distance (MD) statistic is applied to all the scores, obtaining a model based upon the range of the distances that form an ellipsoidal centroid around all the scores (see FIG. 7). Only one group is required to build the model. The other groups are used to establish the relative "goodness of fit" as to how well the model recognizes LP samples and discriminates against the other diseased tissue samples.

Figure 9:
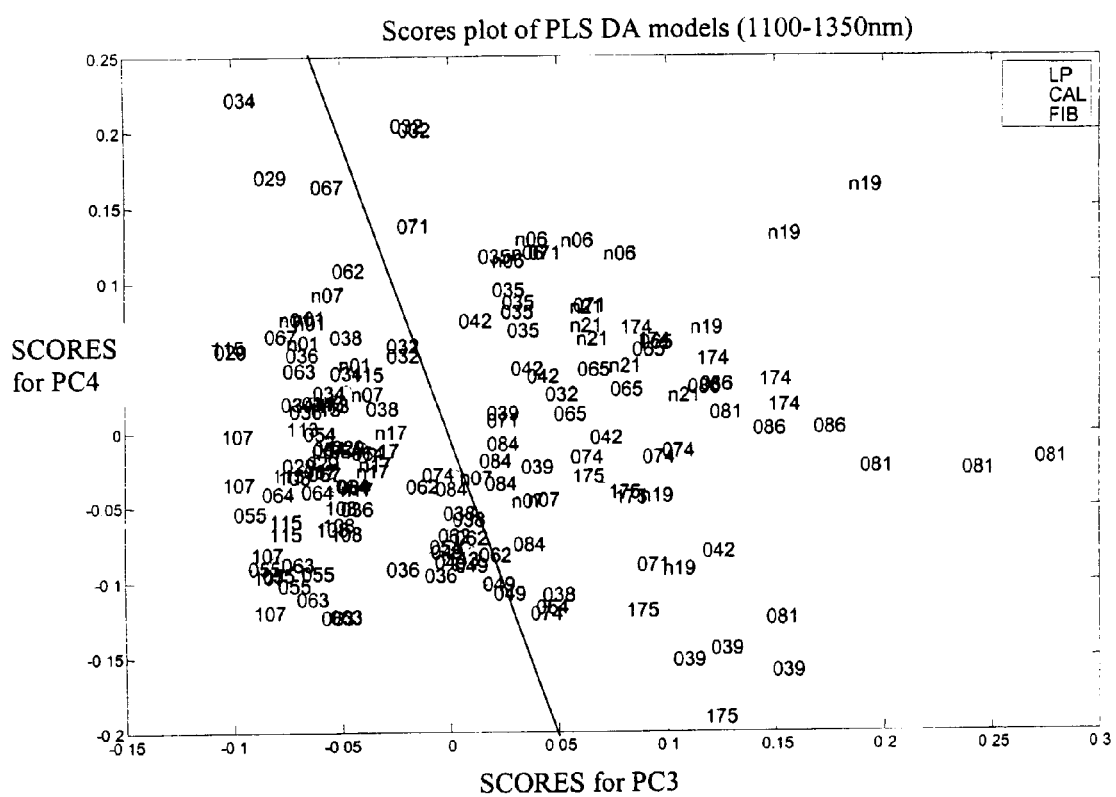
FIG. 9 is a plot of a partial least squares-discriminate analysis (PLS-DA) model of PCA scores between 1100 and 1350 nm. A line is drawn to best separate the scores from the lipid pool samples (LP) from those of all other samples (in this case they were the calcific (CAL) and the fibrotic (FIB) sample scores).

In the second case, PLS-DA, there is a requirement for two groups to be established that are the hardest to distinguish between. These two groups are required to build the model, and the method calculates a "best-fit" line that separates the PCA scores of the LP specimens from the PCA scores of the second group, and in this case the group is the combined FIB and CAL specimen. FIG. 9 is a plot of the results of the PLS-DA model of PCA scores between 1100 and 1350 nm. In this case, a linear discrimination line was used to separate the principal component scores for factor 3 (PC3) from the principal component scores from factor 4 (PC4), where a "factor" is the vector describing the largest influence remaining in the spectral matrix. A best-fit line was drawn to best separate the scores from the lipid pool samples (LP) from those of all other samples (in this case they were the calcific (CAL) and the fibrotic (FIB) sample scores).

To determine how well a model works, separate groups of samples classified by morphology were set aside and used as a validation test set, LP samples not used to build the model were used in the validation step. Sensitivity (SENS) is the ability to recognize a sample that is the same as the model, lipid pool samples in this case and Specificity (SPEC) is the ability of the model to disregard samples that are not the same as the model (NML, CAL, FIB, etc). The reported SENS and SPEC values were comprised of the percentage of the number of LP samples that passed (in the case of SENS) or failed (in the case of SPEC), and in the case of the PCA/MDR model there is a the three parameter tests of the model: (1) the model Mahalanobis Distance boundaries, (2) the score limits, and (3) the residual limits. Both the SENS value and the SPEC values should be close to 100% for the better models, indicating that the model can classify all of the LP samples as LP and reject all other groups tested.

As discussed in further detail in Example 1 below, human aorta tissue samples were analyzed and characterized using standard histology and morphology techniques. As described in Example 2, each sample was subjected to NIR spectroscopy and the resulting reflectance spectra were collected, analyzed, and categorized into large data sets (Example 3).

EXAMPLES

The invention is further described in the following examples, which do not limit the scope of the invention described in the claims.

Example 1

Human Aorta Tissue Sample Preparation

Human aortic tissues were obtained from the thoracic or abdominal region of deceased patients and removed 24 hours or less after death. The tissue samples were stored at 4° C. in saline solution or a phosphate buffered 0.9% saline (PBS) solution. The aortas contained multiple, advanced atherosclerotic lesions unless specifically chosen as normal samples. The aortic fat was removed from the exterior of the aortic vessel. Each specimen (plaque or normal) was removed from the aorta using a 2 cm block template with the plaque or normal region centered within the block and kept moist until the near infrared (NIR) experiments were finished. The plaque sample was oriented such that the maximum lipid pool area was horizontally located in the center of the specimen. Once the NIR spectroscopy experiment was performed, the tissue specimen was placed in a sample holder with the upper left hand corner of the tissue laid in the upper left hand corner of the sample holder. A digital photograph was taken of the entire specimen.

Example 2

Analytical Sample Setup

A NIR spectrum was obtained from each human aortic sample using a FOSS® NIRSystem®, model 6500, with a hand held ½ inch fiber optic probe attachment held in place on a vertical stage adjustment platform. VISION® software version 2.11 data acquisition software was used to collect the spectrum and convert the data from Reflectance to Absorbance units. The recorded wavelength range spanned from 400 nm to 2500 nm acquiring 32 co-added scans at a 10 nm resolution. Data acquisition took 45 second per sample.

Figure 10:
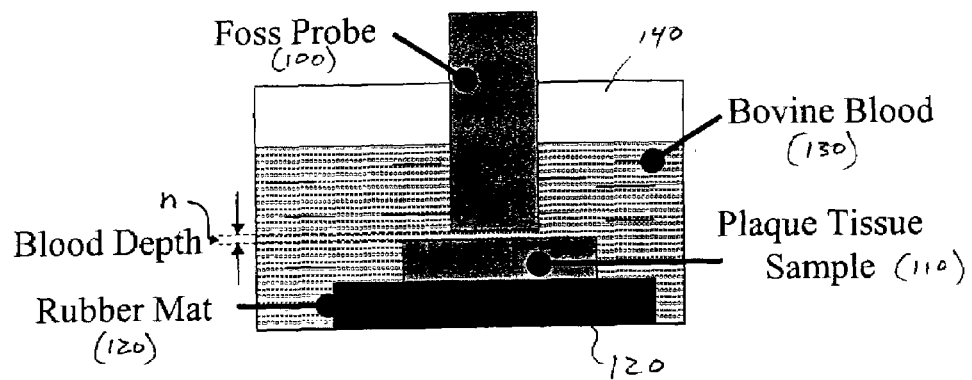
FIG. 10 is a schematic diagram of the NIR spectroscopy experimental setup.

As shown in FIG. 10, an experimental setup was created to hold the fiber optic probe in place at all times during the experiment. A FOSS® probe 100 was located vertically above the plaque tissue sample 110, which is positioned on a rubber mat or pad 120. The sample was illuminated through bovine blood 130. The distance between probe 100 and the sample 120 is the "blood depth n."

A Z-stage micrometer (not shown) was added to the platform to regulate the vertical adjustments of the FOSS probe 100 and to measure the distance from the surface of the sample (zero point) and upwards at 0.25, 0.5, 1.0, 1.5, 2.0, 2.5, and 3.0 mm increments. The specimen was placed on the center of a 4×4×0.5 $cm^3$ black rubber pad 120. The aortic sample 110 with the intimal side facing up was fixed over the rubber with pins at all four corners, and then placed in a small PYREX® dish 140 that holds up to 100 ml of liquid. The sample dish was then placed into a recirculating heated water bath set to 38° C. as monitored by a mercury thermometer.

The optical FOSS® probe was adjusted until it contacted the top of the plaque (or normal) sample and the micrometer was set to zero (0). For each of the probe placements the data acquisition was performed twice without moving the probe. The sample was first scanned in air at the zero mark and then the probe was raised to 2 mm and scanned again. A solution of 0.9% saline (warmed to 38° C.) was then poured into the glass dish immersing both the sample and probe to a height well above 10 mm. The sample was scanned and then the saline was removed using a syringe, without moving the sample or the dish.

Fresh 40% hematocrit bovine blood anti-coagulated with heparin (warmed to 38° C.) was placed in the PYREX® container up to a height of about 15 mm. The probe was lowered back to the zero position (0 mm on the micrometer) and the sample was then scanned in the bovine blood. The probe (using the micrometer) was moved to 0.25 mm and the sample was again scanned, the process repeated for 0.5, 1.0, 1.5, 2.0, 2.5 and 3.0 mm distances between the probe tip and the tissue sample.

All the digital data files were converted from Reflectance to Absorbance and then stored. All of the NIR spectra were visually inspected for data consistency using the VISION® software. Certain data sets were then excluded from further use based on 1) all spectra within a data set did not change with respect to the depth changes, and 2) some samples within a data set changed with respect to depth and other did not.

The results are shown in FIG. 4A, which displays a lipid pool plaque sample at various sample-to-probe distances. FIG. 4B is a plot of the same data shown in FIG. 4A, but the data was offset (normalized) by the absorbance at 1125 nm for each spectrum, showing differences that exist between the samples.

Example 3

Morphological and Morphometric Analysis to Create Data Sets

After processing by NIR spectroscopy, the samples were fixed overnight in a 3% formalin solution. Samples that showed gross evidence of calcification were decalcified in 5% HCl in formalin for 4 hours following formalin fixation.

Figure 11:
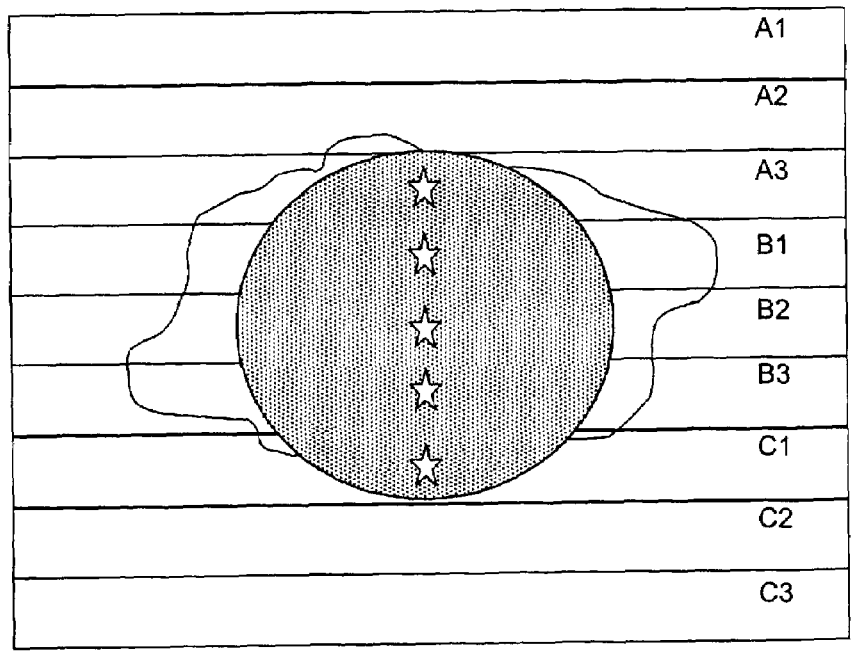
FIG. 11 is a schematic diagram of the histology layout used for processing the tissue specimen. Nine segments were sliced by hand (labeled A1 through C3) with the segments subtended by the FOSS® probe illumination circle (center circle) of most importance (segments A3, B1, B2, B3, C1) in the analysis. The stars indicate the approximate center of each of the segments where the slices for slides were taken to avoid edge effects from the gross cutting.

Sectioning of the specimens was done by hand with a scalpel into three segments, and those three segments were divided (again by hand) into three subsections and placed within paraffin for sectioning. The slides were made from the approximate middle of the subsections at 500 to 750 microns into the block. For the suspected plaque lesion samples, several ribbons were taken from the following subsections: the centermost piece, and the four edge pieces that touch the center piece. FIG. 11 is a schematic diagram of the histology layout used for processing the tissue specimen. Nine segments (labeled A1 through C3) were removed, with the segments subtended by the FOSS® probe illumination circle (center circle) of most importance (segments A3, B1, B2, B3, C1) in the analysis. The stars indicate the approximate center of each of the segments from which the slices for slides were taken to avoid edge effects from the gross cutting. For the normal specimens only the center, and two outer pieces were analyzed (see FIG. 11, segments A3, B2, C1).

Five slides were made for staining purposes, two using H&E and two using Trichrome-Elastin and one spare blank slide. There were 25 slides for each plaque sample and 15 slides for each normal sample. One staining set was produced for planimetry analysis using all the slices, and another set was made for initial morphology analysis using only the centermost B2 slices.

The morphology (or overall description) for each specimen was characterized from the histology of the stained slides for each of the subsections. Within each slide subsection, only the area illuminated by the FOSS® probe was considered in the analysis (see central circle in FIG. 11). The probe diameter was ½ inch (1.27 cm), but the actually projection area used for histology was approximated as a 1 cm diameter circle within the center of the tissue sample to approximate tissue shrinkage and light scattering events during the NIR analysis.

The initial morphology of the samples was performed based upon accepted descriptions of normal and vulnerable plaque tissues established by Virmani et al at the Armed Forces Institute of Pathology (AFIP) Arteriosclerosis. Thromb. Vasc. Biol., 2000, 20:1262. Plaque samples were further separated into lipid pool, fibrous, or calcific plaques with the extremes being classified as having the majority of the main constituent within the probe illumination area. Approximate lipid pool width and depth along with average and minimum cap thickness were also recorded for most of the lipid pool samples.

Computerized morphometry (planimetry) was performed for all the stained tissue slices. The morphometric analysis was used to determine the Total Plaque Area (subtended by the FOSS probe) then separated out into Total Lipid Pool Area, % Lipid Pool Area to Total Plaque Area, and Cap Thickness (measured at the thinnest region only). Further, cap thickness measurements were obtained for all the data samples that contained lipid pools. The average cap thickness was measured over the center 10 mm of the centermost section to provide an average cap thickness value.

The normal samples were also analyzed to determine if the tissue of the outer subsections were free of disease. Any start of disease or lipid pool found in the segments disqualified the specimen as normal. The normal samples were from individuals that ranged in age from as young as 29 up to 87 years of age. Most of the normal samples came from individuals that did not have any disease.

Samples selected for the study represented the diseased plaques of LP, FIB, or CAL along with the NML tissue, all within the FOSS probe subtended area. The LP samples selection was based upon the size of the total plaque area (only the larger plaques were used to build the model) and the ratio of the mean Cap Thickness to the percentage of LP area and the percentage of the LP area to total plaque area (smaller caps on larger LP plaques were ranked as good LP extreme samples).

Example 4

Data Set Development

A subset of the full data set was formed using the histology analysis as described in Example 3.

The data was segmented out by the two pathologists and then classified as extreme classification samples. The extremes were classified as consisting predominately of one disease component, without regard to the thickness of the cap on the lesion. The full dataset contained a total of 207 samples with 194 usable. The files used for modeling were chosen using two criteria: (i) being in the top ⅓ largest plaques in the sample set, and (ii) the average cap thickness (in microns), in a ratio to the percent lipid pool area to the total diseased plaque area. This threshold was set to be less than 18, determined as the middle of the histogram plot of all the data. This filter process resulted in a total of 33 extreme plaques and 27 Normal (NML) samples. The plaque samples were further classified as 16 Lipid Pool (LP), 8 Calcific (CAL), and 9 Fibrotic (FIB).

To increase the number of plaque samples in the model, 2 lipid-filled disrupted plaque (DP) samples were added to the calibration set and another 2 lipid-filled DP samples to the validation set. This increased the number of LP samples to 10 samples per each set, validation, or calibration. These DP plaque samples were chosen because they were large in size, had very thin to non-existent caps, and still retained a large amount of pooled lipid within the plaque.

Example 5

Determination of the Wavelength Range of 1100 to 1415 nm

The final method used to evaluate the data sets was the linear regression model based upon the Mahalanobis Distance and the scores from the PCA decomposition, the PCA/MDR method. Within the different regions tested, most predictive regions were found to cluster in the region from about 1100 to 1415 nm, and more particularly from about 1150 nm to 1350 nm, about 1175 to 1280, and about 1190 to 1250 nm. The data were first preprocessed for scatter removal using Standard Normal Variant (SNV) with Mean Centering (MC). Overall the SNV with MC preprocessing option provided the best SENS and SPEC results for all models tested as compared to no preprocessing, mean centering, first derivative, second derivative, and other preprocessing options tested. The best band regions found for the dual 30 nm test were from 1175 nm to 1205 nm combined with 1310 nm to 1340 nm, and 1145 to 1175 nm combined with 1250 to 1280 nm. 88% of the LP samples fit the model first model with 86% of the FIB and CAL samples, and 100% of the NML samples were rejected by the model. For the second set of bands, 90% of the LP samples fit the model and 86% of the FIB and CAL samples, and 86% of the NML were rejected by that model.

Specifically, the PCA/MDR model was used to determine the range of configurations that could be used for discriminating plaques containing mainly lipid pool from other disease types and also non-disease types. A minimum of two selected wavelengths or one or more narrow wavelength bands (e.g., one wavelength and one narrow band) within the wavelength range of 1100 to 1415 nm are required. Either continuous or discontinuous wavelengths or regions can be used to build the model without restriction to size. Many PCA/MDR models were made using the data files for the specimens containing mainly lipid pool and discriminated against fibrotic and calcific lesions together, and then the normal tissue, while also encompassing the variations of the spectra as seen through blood as the probe is progressively moved away from the tissue. The assessment of the models that were tested were obtained from the prediction results of all the plaque types, with a tissue to probe separation value from 0.0 mm to 3.0 mm (see FIG. 4), which represent the expected range of distances between the examination device and the tissue being examined in vivo. Larger distances can also be examined.

The calibration model testing process was repeated eight times with randomly chosen lipid pool samples each time. Each repeated calibration process was averaged over all the regions tested providing the Mean Performance results. These results are displayed in the "projection plots" in FIGS. 8A to 8C for model spectra that were preprocessed using Standard Normal Variant (SNV) and Mean Centering (MC). From those results, the regions from 1100 nm to 1415 nm and a combination of bands from the 1100 nm to 1415 nm region in conjunction with bands in the about 1650 nm to 1780 nm regions (e.g., 1650 to 1730 nm) resulted in many useful models. Each model prediction result was captured as the number of the test lipid pool samples predicted to be part of the model (i.e., vulnerable plaque), and the number of calcific and fibrotic, and then normal tissue samples (i.e., safe plaque), that were excluded from the model, and reported as Percent Sensitivity and Percent Specificity1 and Percent Specificity2, respectively.

Figure 8A:
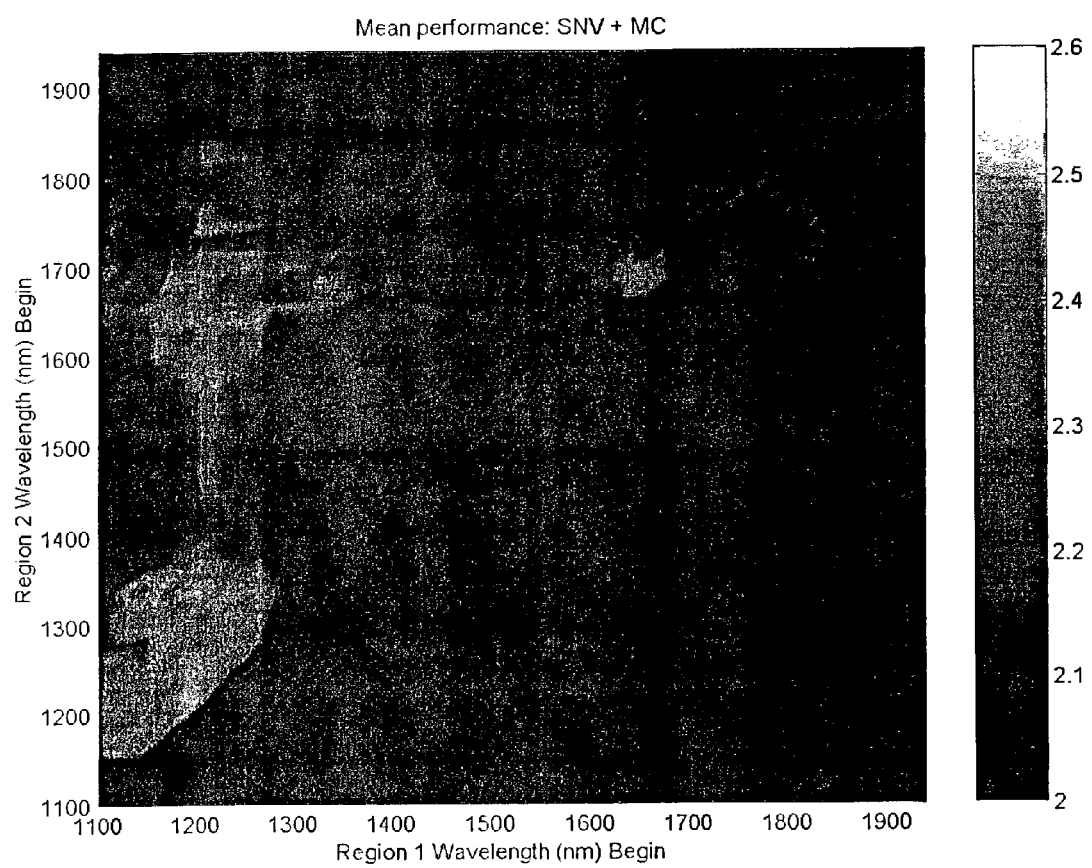
FIG. 8A is a "projection plot" representing the mean prediction performance results from multiple calibration models using two separate 30 nm band regions and preprocessed using SNV plus MC. Specific areas of high Mean Performance occur in the lighter shaded areas and in particular in the regions from 1100 nm to 1415 nm.
Figure 8B:
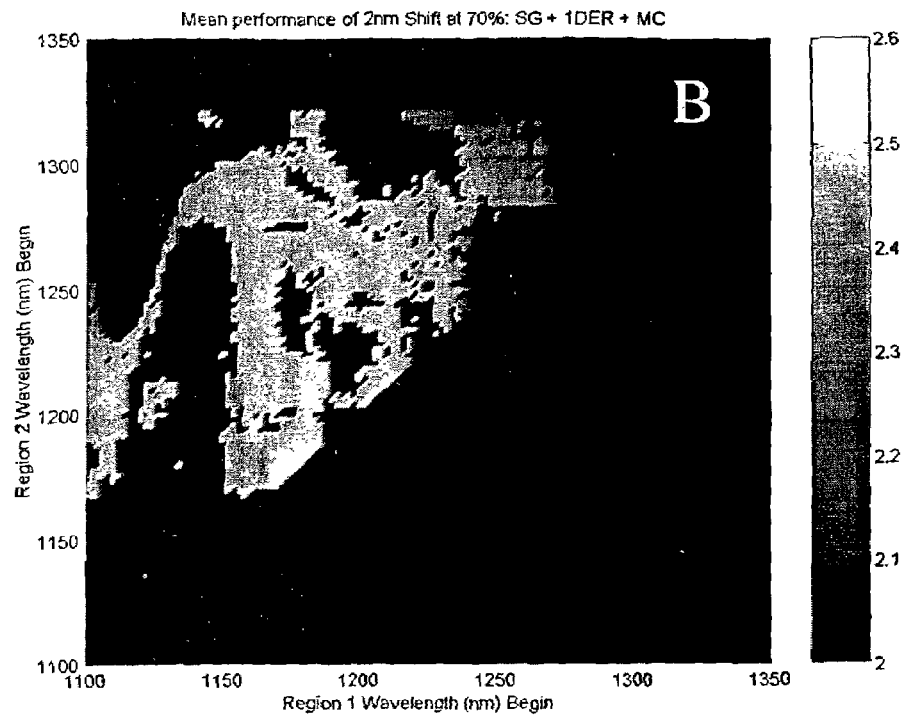
FIGS. 8B and 8C are two additional projection plots of the mean performance using two separate 30 nm bands as in FIG. 8A, but tested at a higher resolution of 2 nm intervals and spanning the region from 1100 nm to 1350 nm. The highest Mean Performance for FIG. 8B occurred in the lighter shaded areas and in particular in the region from 1150 nm to 1250 nm, and for FIG. 8C, the region spanned from 1175 nm to 1280 nm.
Figure 8C:
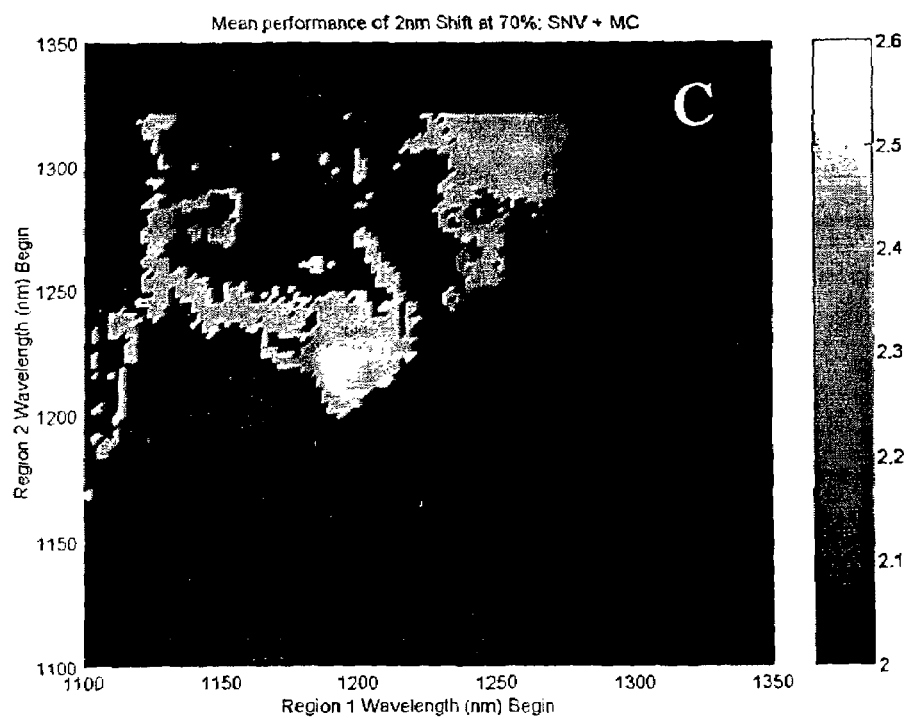

These results were combined as a single metric to generate FIGS. 8A to 8C, in which the x-axis plots the beginning value of the first 30 nm window region and the y-axis plots the beginning value of the second 30 nm window region used in model.

To generate FIG. 8A, two moving "windows" of 30 nm each were tested spanning from 1100 nm to 1850 nm at 15 mm intervals. The X-axis plots the beginning value of the first 30 nm window region and the Y-axis plots the beginning value of the second 30 nm window region used in the model. Only those results greater than 1.8 (equivalent to a minimum response of 60% sensitivity with respect to lipid pool samples not used to build the model, 60% specificity with respect to calcific and fibrotic samples combined, and 60% specificity with respect to the normal samples) were retained. The best result would be 3.0 corresponding to 100% sensitivity and specificity for all groups. Specific areas of high Mean Performance occur in the lighter shaded areas and in particular in the regions from 1100 nm to 1415 nm, and more particularly, 1100 to 1350 nm. Areas of higher Mean Performance occur in the most lightly shaded (highlighted) areas and in particular in the region from 1190 nm to 1250 nm.

FIGS. 8B and 8C are two projection plots of the mean performance using two separate 30 nm bands as in FIG. 8A, but tested at a higher resolution of 2 nm intervals and spanning the region from 1100 nm to 1350 nm. The X-axis plots the beginning value of the first 30 nm window region and the Y-axis plots the beginning value of the second 30 nm window region used in model. A higher threshold was applied to this data (compared to FIG. 8A) so that only those models where the minimum retained value for sensitivity with respect to lipid pool samples was 70%, for specificity with respect to calcific and fibrotic samples combined was 70%, and for specificity with respect to the normal samples was 70%. The best result would be 3.0 corresponding to 100% sensitivity and specificity for all groups and the minimum would be 2.1.

In FIG. 8B, the data was first pretreated using a Savitsky-Golay smoothed first derivative followed by mean centering, and in FIG. 8C the data was first pretreated using Standard Normal Variate with mean centering. The highest Mean Performance for FIG. 8B occurred in the lighter shaded areas and in particular in the regions from about 1150 nm to 1250 nm, and for FIG. 8C, the region spanned from about 1175 nm to 1280 nm.

For example, one embodiment uses two 30 nm band regions that are discontinuous in the region from 1190 nm to 1290 nm as seen in FIGS. 8B and 8C by the grey areas within the very light white region from 1190 to 1290 nm. Another embodiment uses bands from 1175 to 1205 nm with 1310 to 1340 nm. Alternatively, another embodiment uses bands from 1145 to 1175 nm with 1250 to 1280 nm.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An in vivo method for characterizing plaque composition in a blood vessel wall, the method comprising
   (a) through whole blood, illuminating a tissue in the blood vessel wall with any two or more single wavelengths or one or more narrow wavelength bands of near-infrared radiation within a wavelength range of about 1100 to 1415 nm;
   (b) through whole blood, detecting radiation reflected from the tissue, the radiation having a wavelength of from about 1100 to 1415 mn;
   (c) processing the detected radiation to characterize the plaque composition; and
   (d) providing an output indicative of the characterization of the plaque composition.

2. The method of claim 1, wherein the one or more narrow wavelength bands each span about 1.0 nm to about 100 nm within the wavelength range of 1100 to 1415 nm.

3. The method of claim 1, wherein two single wavelengths are used.

4. The method of claim 1, wherein two narrow wavelength bands, each spanning 1.0 nm to 30 nm within the wavelength range of 1100 to 1415 nm are used.

5. The method of claim 1, wherein at least one narrow wavelength band and at least one single wavelength are used.

6. The method of claim 1, wherein the wavelength range is about 1100 to 1350 nm.

7. The method of claim 1, wherein the wavelength range is about 1150 to 1250 nm.

8. The method of claim 1, wherein the wavelength range is about 1175 to 1280 nm.

9. The method of claim 1, wherein the wavelength range is about 1190 to 1250 nm.

10. The method of claim 1, further comprising illuminating the tissue in the blood vessel wall with any two or more single wavelengths or one or more narrow wavelength bands of near-infrared radiation within a second wavelength range of about 1600 nm to 1780 nm; and further detecting radiation reflected from the tissue having a second wavelength of from about 1600 nm to 1780 nm.

11. The method of claim 10, wherein the second wavelength range is about 1650 to 1730 nm.

12. The method of claim 1, wherein the processing is done using chemometric discrimination algorithms.

13. The method of claim 1, further comprising preprocessing the detected radiation to remove spectral information not related to a characterization of the tissue.

14. The method of claim 1, wherein the blood vessel is an artery.

15. The method of claim 1, wherein the blood vessel is a coronary artery.

16. The method of claim 1, wherein the tissue comprises a lipid pool.

17. The method of claim 1, wherein the tissue comprises a lipid pool and a thin fibrous cap.

18. The method of claim 1, wherein the tissue comprises a lipid pool and a thick fibrous cap.

19. The method of claim 1, wherein the tissue comprises fibrotic or calcific tissue.

20. An apparatus for characterizing plaque composition within a blood vessel containing whole blood, said apparatus comprising:
a near-infrared radiation source that generates radiation for illumination of tissue through blood, the radiation comprising any two or more single wavelengths or one or more narrow wavelength bands of near-infrared radiation within a wavelength range of about 1100 to 1415 nm, the radition being sufficient to penetrate whole blood;
one or more radiation conduits for transmitting radiation from the radiation source, through whole blood, to the tissue and for receiving radiation not absorbed by the tissue;
a radiation detector that collects radiation not absorbed by the tissue across a wavelength range of substantially 1100 to 1415 nm, the radiation detector having a sensitivity sufficient to detect the radiation after the radiation has been attenuaded by whole blood;
a processor that processes the collected radiation to determine the composition of plaque in the tissue; and
an output device for providing output characterizing the plaque composition.

21. The apparatus of claim 20, wherein the near-infrared radiation source generates a wavelength range of about 1100 to 1350 nm.

22. The apparatus of claim 20, wherein the near-infrared radiation source generates two narrow wavelength bands, each spanning 1.0 nm to 30 nm within the wavelength range of 1100 to 1415 nm.

23. The apparatus of claim 20, wherein the near-infrared radiation source generates a wavelength range of about 1150 to 1250 nm.

24. The apparatus of claim 20, further comprising a near-infrared radiation source that generates radiation comprising any two or more single wavelengths or one or more narrow wavelength bands of near-infrared radiation within a second wavelength range of about 1600 to 1780 nm.

25. An instrument for in vivo characterization of plaques, the instrument comprising
a) means for illuminating plaques through whole blood, the means for illuminating using near-infrared radiation comprising any two or more single wavelengths or one or more narrow wavelength bands of near-infrared radiation within a wavelength range of about 1100 to 1415 nm;
b) means for collecting radiation through whole blood, the radiation being within the wavelength range that is not absorbed by the plaques;
c) means for determining, from the collected radiation the amounts of absorbance of radiation by the illuminated plaques; and
d) means for discriminating one illuminated plaque from another illuminated plaque within the wavelength range, wherein the discriminating means comprises
i) means for preprocessing the absorbance amounts using a chemometric preprocessing technique, and
ii) means for performing a chemometric discrimination algorithm on the preprocessed absorbance amounts to characterize the plaques; and
e) means for providing an output indicating the characterization of plaque composition.

26. A method for in vivo characterization of plaque in blood vessel walls utilizing a fiber optic probe, the method comprising:
introducing the probe into a blood vessel;
directing, throught whole blood between the probe and the wall and onto a plaque in the blood vessel wall, near-infrared radiation comprising any two or more single wavelengths or one or more narrow wavelength bands within a wavelength range of about 1100 to 1415 nm;
throught whole blood, detecting radiation not absorbed by the blood vessel wall, the detected radiation having a wavelength within the range of substantially 1100 to 1415 nm: and
analyzing the detected radiation to categorize the plaque in the blood vessel wall.

27. An in vivo method for characterizing a plaque in a blood vessel wall, the method comprising:
(a) through whole blood, illuminating a plaque in the blood vessel wall with any two or more single wavelengths of near-infrared radiation within a wavelength range consisting of wavelengths from about 1100 nm to about 1415 nm;
(b) detecting, through whole blood, radiation reflected from the plaque, the reflected radiation having a wavelength of from about 1100 to 1415 nm;
(c) processing the detected radiation to characterize the plaque in the blood vessel wall; and
(d) providing an output indicating the plaque characterization.

28. The method of claim 1, wherein illuminating a plaque comprises scanning the tissue with having a wavelength that varies between two wavelengths within the range of about 1100 to 1415 nm.

29. An in vivo method for characterizing plaque composition of a plaque in a blood vessel wall, the method comprising:
(a) through whole blood, illuminating a tissue in the blood vessel wall with any two or more single wavelengths of near-infrared radiation from within a particular wavelength range;
(b) through whole blood, detecting radiation reflected from the tissue, the reflected radiation having a wavelength within the particular wavelength range;
(c) processing the detected radiation to characterize the plaque in the blood vessel wall; and
(d) providing an output indicating the characterization;
wherein the particular wavelength range consists of wavelengths between about 1100 nm and about 1415 nm.

30. An in vivo method for characterizing plaque in a blood vessel wall, the method comprising:

selecting a plurality of single wavelengths from a first band that consists of wavelengths between 1100 nm and 1415 nm;

through whole blood, illuminating a plaque on the blood vessel wall with NIR having the wavelengths selected from the first band;

through whole blood, detecting radiation reflected from the plaque, the detected radiation having a wavelength from within the first band;

processing the detected radiation to characterize the plaque; and providing an output indicative of the plaque characterization.

* * * * *